United States Patent [19]

Vinogradoff

[11] Patent Number: 4,644,065

[45] Date of Patent: Feb. 17, 1987

[54] PROCESS FOR THE PREPARATION OF 4(3H)-QUINAZOLINONES

[75] Inventor: Anna P. Vinogradoff, Concord, Calif.

[73] Assignee: Merrell Dow Pharmaceuticals Inc., Cincinnati, Ohio

[21] Appl. No.: 610,456

[22] Filed: May 15, 1984

[51] Int. Cl.$^4$ .................. C07D 403/04; C07D 491/04; C07D 257/04
[52] U.S. Cl. .................................... 548/251; 564/245; 544/250; 544/284; 544/290; 544/289
[58] Field of Search ................ 548/251; 544/284, 289, 544/290; 564/245

[56] References Cited

U.S. PATENT DOCUMENTS 3,284,289 11/1966 Duevv et al. ...................... 564/245
3,539,631 11/1970 Pallos et al. ......................... 564/245
3,696,102 10/1972 Cronin ................................ 544/289

FOREIGN PATENT DOCUMENTS 1809174 6/1970 Fed. Rep. of Germany.
1093977 12/1967 United Kingdom ................ 544/290

OTHER PUBLICATIONS

Patai (Ed.) The Chem. of Amidines and Imidates, pp. 451 & 452, Wiley, N.Y., N.Y. (1975).
A. Arques et al., *Anales de Quimica*, 156 (1982).
L. A. Errede, *J. Org. Chem.*, 41, 1763 (1976).
L. A. Errede, et al., *J. Org. Chem.*, 41, 1765 (1976).
L. A. Errede, et al., *J. Org. Chem.*, 42, 12, 656 (1977).
C. H. Foster, et al., *J. Org. Chem.*, 41, 2646 (1976).
R. A. Henry, et al., *J. Am. Chem. Soc.*, 76, 926 (1954).
P. R. Levy, et al., *J. Chem. Soc.*, 1956, 985.
S. Rajappa, et al., *Tetrahedron*, 29, 1299 (1973).
W. Ried, et al., *Chem. Ber.*, 95, 3042 (1962).
W. Ried, et al., *Ann. Chem.* 707, 250 (1967).
N. A. Vaidya, et al., *J. Org. Chem.*, 47, 1777 (1982).

*Primary Examiner*—Richard L. Raymond
*Assistant Examiner*—D. B. Springer
*Attorney, Agent, or Firm*—John J. Kolano

[57] ABSTRACT

A new process for the preparation of 3-(1H-tetrazol-5-yl)-4(3H)-quinazolinones from anthranilic acid derivatives is described herein. Additional reactants used in the process are 4-aminotetrazole and a trialkoxymethane or the reaction can be carried out using the imidic ester obtained from these two compounds.

11 Claims, No Drawings

PROCESS FOR THE PREPARATION OF 4(3H)-QUINAZOLINONES

BACKGROUND OF THE INVENTION 3-(1H-Tetrazol-5-yl)-4(3H)-quinazolinone and related compounds have been described in U.S. Pat. No. 4,419,357 as useful as mediator release inhibitors. The compounds are prepared by a several-step procedure starting with an appropriate 2-nitrobenzoyl chloride. The indicated acid chloride is reacted with 5-aminotetrazole to give the corresponding carboxamide and the nitro group is then reduced to give the corresponding 2-amino-N-(1H-tetrazol-5-yl)benzamide. This benzamide is then heated with triethoxymethane to give the quinazolinone referred to originally. This procedure is generally similar to one described in the literature for preparing other related quinazolinones. While this method may ordinarily be adequate for obtaining the compound in question, it does suffer from a number of disadvantages, particularly when larger supplies of compound are desired. Thus, the nitrobenzoyl chloride starting material used in the original procedure is relatively expensive and reactive; solids handling problems are involved with the intermediates in question and the overall yield is only about 50%.

Other different methods for the preparation of substituted 4(3H)-quinazolinones have been described in the literature and one general approach makes use of anthranilic acid derivatives. Thus, Levy et al., *J. Chem. Soc.*, 1956, 985, describes the reaction of methyl anthranilate with a benzimidoyl chloride to give a quinazolinone. A number of intermediates are suggested although they are not specifically isolated. A similar procedure is described in Bayer German Pat. No. 1,809,174, although the intermediates proposed there are not the same as those set forth by Levy et al. In both of these procedures, however, the benzimidoyl chloride used as a starting material would be relatively stable and easy to prepare as compared to the intermediate formimidoyl chloride which would be needed to prepare the tetrazolyl compounds mentioned earlier. Actually, it is questionable whether the appropriate formidoyl compound could be obtained at all for the indicated tetrazole series.

In a somewhat different approach, Rajappa et al., *Tetrahedron*, 29, 1299 (1973), describes the reaction of anthranilic acid with a bicyclic imino ether to give a complex tetracyclic system which contains the quinazolinone structure. Rajappa et al., were interested in other questions and provided no details with regard to this process or any background leading up to their use of it. It is noted, however, that their process was limited to the acid (anthranilic) and heat alone was sufficient to bring about the cyclization involved in the preparation of the Rajappa compounds.

Finally, in a still different approach, Arques et al., *Anales de Quimica*, 156 (1982), describes the reaction of methyl anthranilate first with the dimethylacetal of dimethylformamide followed by an amine to give a 3-substituted 4(3H)-quinazolinone. Arques also provides a brief summary of other methods for preparing 4(3H)-quinazolinones.

SUMMARY OF THE INVENTION

A new procedure for the preparation of 4(3H)-quinazolinones has been found which is particularly suitable for the preparation of the tetrazolyl quinazolinones referred to initially. This procedure is convenient and it gives the desired compounds in good yields. The quinazolinones involved are acidic and form salts with alkali metals, ammonia and amines. Such salts are equivalent to the free tetrazoles and they can also be obtained by the present procedure. Specifically, the procedure involves a process for the preparation of quinazolinones of the formula

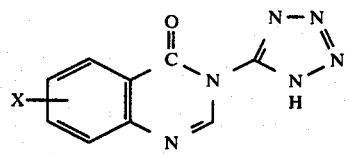

wherein X represents hydrogen or one or two methyl, halogen or methoxy groups or a methylenedioxy group, and the alkali metal, ammonium and amine salts thereof, which comprises:

(a) Reacting an anthranilic acid derivative of the formula

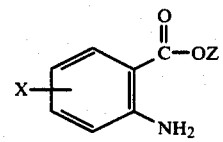

wherein X is defined as above and Z is alkyl of 1-4 carbon atoms or ammonium or OZ is $NH_2$; with a 5-(alkoxymethyleneamino)tetrazole which has the structural formula

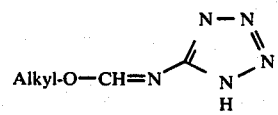

wherein the Alkyl group contains 1 to 4 carbon atoms, in an inert solvent to give a formamidine of the formula

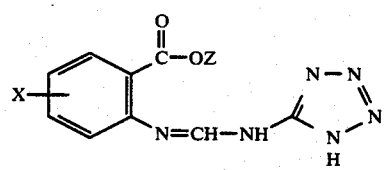

(b) Cyclizing said formamidine to the quinazolinone product directly when Z or OZ contains nitrogen or, when Z is alkyl of 1-4 carbon atoms, by the use of an alkali metal base, ammonium hydroxide or an amine and, (c) When the cyclization product is obtained in the form of a salt and the free tetrazole is desired, acidifying said cyclization product with a mineral acid to give the desired quinazolinone.

The amines referred to above with regard to salts or the cyclization are mono-, di- and tri-alkylamines wherein each alkyl group contains up to four carbon atoms.

The present invention further encompasses the novel imino ether and formamidine intermediates used in the present process.

Thus, it has been found that 3-(1H-tetrazol-5-yl)-4(3H)-quinazolinone and related compounds (Formula I) can be obtained readily from certain anthranilic acid derivatives (Formula II) and an appropriate imino ether of 5-aminotetrazole (Formula III). This gives the corresponding formamidine derivative (Formula IV) which then cyclizes to give the desired quinazolinone product. The tetrazole substituent group is acidic so that when the cyclization reaction is carried out under alkaline conditions or a cation is available in the reaction mixture as a result of the particular anthranilic acid derivative used, the product is obtained as the tetrazole salt. It is then necessary to acidify this salt if the free tetrazole is desired. Mineral acids such as hydrochloric acid are preferred for this acidification.

In the first step of the process, the anthranilic acid derivative and the imino ether (used either as the compound itself or as prepared in situ) are heated in an inert solvent such as carbon tetrachloride, 2-propanol or other solvents and the indicated mixed formamidine forms. When Z or OZ contains nitrogen, the formamidine cyclizes directly to the desired product but, when esters are used (Z is alkyl), it is necessary to treat the formamidine with base either with or without isolation of the formamidine. When Z is alkyl and the formamidine is isolated, it is then treated with base in an appropriate solvent to give the desired quinazolinone. Hydroxylic solvents such as methanol or 2-propanol are preferred although other solvents such as toluene and dimethylformamidine can be used. Bases which can be used in the cyclization step, with or without isolation of the formamidine, include sodium carbonate, sodium hydroxide, sodium methoxide, sodium t-butoxide, ammonium hydroxide, n-propylamine, diethylamine, trimethylamine and triethylamine. As noted earlier, when base is present in the reaction mixture, the product is obtained as the tetrazole salt. Heating is optional for the cyclization step.

The imino ether used in the first step of the process is prepared by heating 5-aminotetrazole and an appropriate trialkoxymethane in excess trialkoxymethane or in an inert solvent such as hexane, carbon tetrachloride or N,N-dimethylformamide. If desired, the imino ether can be specifically isolated and then used in the present process. However, it hydrolyzes rapidly on exposure to atmospheric moisture so that it is usually preferable to prepare the imino ether in situ and use it immediately in the process of the invention. In view of this fact, this reactant may not be named specifically in many of the examples but it is actually formed in the reaction mixture and then reacts further as described. The examples involved should thus be read with this fact in mind.

A preferred embodiment of the present invention involves carrying out the process using anthranilic acid esters (i.e., Z is alkyl of 1–4 carbon atoms). A further preferred embodiment involves the use of methyl anthranilate in the process, with the imino ether prepared in situ and the entire process carried out in a single pot. In this further preferred embodiment of the present invention, specifically directed to the preparation of 3-(1H-tetrazol-5-yl)-4(3H)-quinazolinone, it is possible to combine the preparation of the imino ether with the process described earlier and carry out the complete synthesis of the 3(4H)-quinazolinone without isolating any of the intermediates. Thus, triethoxymethane, 5-aminotetrazole and methyl anthranilate are mixed in an inert solvent and heated. Examples of useful solvents are 2-propanol, carbon tetrachloride, toluene or ethyl acetate. The formamidine described earlier forms in the reaction mixture and base is then added as discussed earlier and the mixture is heated to bring about cyclization and give the desired 4(3H)-quinazolinone. The success of this process is particularly unexpected in that, in spite of the fact that the initial reaction mixture contains two different amine compounds, the triethoxymethane has been found to react selectively with the 5-aminotetrazole to give the corresponding imino ether and this imino ether then reacts readily and cleanly with the amino group of the anthranilic acid ester to give the formamidine described earlier. The process proceeds here to give the indicated compounds in good yields so that it would be a particularly attractive method for preparing the specific compound in question.

It can be seen that the process here is advantageous over that described initially in that anthranilic acid derivatives are more readily available than the 2-nitrobenzoic acid compounds which serve as the starting material in the prior art procedure discussed earlier. In addition, the present synthesis can be completed in much less time than the procedure used originally.

The following examples are presented to illustrate the present invention. They should not be construed as limiting it in any way.

EXAMPLE 1

A mixture was prepared from 50 g of 5-aminotetrazole, 347 g of triethoxymethane and 500 ml of hexane and this was heated under nitrogen so that distillation took place at a moderate rate (head temperature about 60°–68° C.). Distillate was collected over a period of 6 hours with hexane being replaced in the reaction mixture as necessary. The mixture was then cooled to room temperature and the fine white needles that formed were collected by filtration, washed with hexane and vacuum oven dried with heating to give 5-(ethoxymethyleneamino)tetrazole. This material hydrolyzes rapidly on exposure to atmospheric moisture so that it should be used promptly for any further reactions desired or it should be stored using appropriate conditions.

EXAMPLE 2

A mixture of 10 g of 5-aminotetrazole, 18 g of triethoxymethane and 200 ml of carbon tetrachloride was heated under nitrogen with stirring until distillate appeared. Then, a moderate rate of distillation was maintained for 6 hours with carbon tetrachloride being replaced in the reaction mixture as necessary. At this point, analysis of the crystals present showed complete conversion of aminotetrazole. The white crystals were then filtered from the hot solution and washed briefly with carbon tetrachloride to give a wet cake of 5-(ethoxymethyleneamino)tetrazole which was used immediately as is.

EXAMPLE 3

A mixture of 25 g of 5-aminotetrazole monohydrate and 356 g of triethoxymethane was heated under nitrogen with stirring at 100° C. for 4 hours during which time a distillate was collected. Then, 30 ml of cyclohexane was added and the mixture was cooled first to room temperature and then briefly with an ice-water bath. The white crystals which formed were separated by filtration and vacuum oven dried to give 5-(ethoxymethyleneamino)tetrazole.

EXAMPLE 4

A mixture was prepared from 12.2 g of 5-aminotetrazole monohydrate, 71.3 g of triethoxymethane, 22.3 g of methyl anthranilate and 100 ml of carbon tetrachloride and this was refluxed under nitrogen with stirring for 16 hours. The mixture was then cooled to room temperature and the white crystals which formed were separated by filtration, washed with carbon tetrachloride and dried to give $N^1$-(1H-tetrazol-5-yl)-$N^2$-(2-carbomethoxyphenyl)formamidine melting at about 199°–200° C.

EXAMPLE 5

A mixture of 5 g of 5-aminotetrazole and 150 ml of 2-propanol was heated to 80° C. under nitrogen. To the resulting heterogeneous mixture was added 7 g of trimethoxymethane and 9.3 g of methyl anthranilate. The mixture was stirred for 35 minutes and then cooled to 30° C. The white crystals which formed were separated by filtration, washed with 2-propanol and vacuum oven dried to give $N^1$-(1H-tetrazol-5-yl)-$N^2$-(2-carbomethoxyphenyl)formamidine.

EXAMPLE 6

A mixture was prepared from 9.5 g of 5-aminotetrazole, 16.5 g of triethoxymethane and 50 ml of N,N-dimethylformamide and heated under nitrogen and a solution of 16.9 g of methyl anthranilate in 15 ml of N,N-dimethylformamide was added to the hot mixture and stirred for 15 minutes. The mixture was then cooled to room temperature and stirred for 16 hours. The white crystals which formed were separated by filtration, washed first with N,N-dimethylformamide and then with 2-propanol, and vacuum oven dried to give $N^1$-(1H-tetrazol-5-yl)-$N^2$-(2-carbomethoxyphenyl)formamidine which was identical with authentic material.

EXAMPLE 7

A mixture of 5 g of 5-aminotetrazole, 46.7 g of triethoxymethane, 10.5 g of methyl anthranilate and 105 ml of hexane was heated at reflux under nitrogen for 48 hours. The mixture was cooled to room temperature and the white crystalline product was separated by filtration, washed with hexane and vacuum oven dried to give product containing traces of methyl anthranilate. This was triturated with additional hexane, followed by filtration and drying to give pure $N^1$-(1H-tetrazol-5-yl)-$N^2$-(2-carbomethoxyphenyl)formamidine.

EXAMPLE 8

A mixture of 12.1 g of 5-aminotetrazole monohydrate, 42 g of triethoxymethane, 21 g of methyl anthranilate and 50 ml of 2-propanol was stirred at room temperature under nitrogen for 2 days. The white solid which formed was separated by filtration, washed with 2-propanol and vacuum oven dried to give $N^1$-(1H-tetrazol-5-yl)-$N^2$-(2-carbomethoxyphenyl)formamidine which was identical with authentic material.

EXAMPLE 9

To a mixture of 5 g of 5-(ethoxymethyleneamino)tetrazole in 50 ml of ethyl acetate, stirred at room temperature under nitrogen, there was added a solution of 10.2 g of methyl anthranilate in 50 ml of ethyl acetate and the mixture was stirred for 24 hours. The white solid which formed was separated by filtration, washed with ethyl acetate and vacuum oven dried to give crude $N^1$-(1H-tetrazol-5-yl)-$N^2$-(2-carbomethoxyphenyl)formamidine. This was recrystallized from a mixture of N,N-dimethylformamide and ethyl acetate to give pure product identical with authentic material.

EXAMPLE 10

Methanol (15 ml) was cooled to about 0° C. in an ice-acetone bath and 0.3 g of $N^1$-(1tetrazol-5-yl)-$N^2$-(2-carbomethoxyphenyl)formamidine was added under nitrogen with stirring to give a heterogeneous mixture. Stirring under nitrogen was continued and about 66 mg of sodium methoxide was added portionwise to give a homogeneous solution. Additional sodium methoxide was added to bring the pH to between 7–8. The solvent was then evaporated under reduced pressure to give the sodium salt of 3-(1H-tetrazol-5-yl)-4(3H)-quinazolinone. The product obtained by this procedure was identical in all respects with material prepared by the procedure described in the literature.

EXAMPLE 11

A mixture was prepared from 2.9 g of the sodium salt of 3-(1H-tetrazol-5-yl)-4(3H)-quinazolin-4-one, 25 ml of methanol and 15 ml of water and stirred at room temperature. To this mixture was added 4 ml of 3N hydrochloric acid and stirring was continued for 15 minutes. The white solid which formed was separated by filtration, washed with water and vacuum oven dried to give 3-(1H-tetrazol-5-yl)-4(3H)-quinazolinone which was idential with authentic material.

EXAMPLE 12

A slurry of 3 g of $N^1$-(1H-tetrazol-5-yl)-$N^2$-(2-carbomethoxyphenyl)formamidine in 10 ml of methanol was stirred at room temperature. A solution of 0.8 ml of 14.8M ammonium hydroxide in 5 ml of methanol was added to the mixture which was stirred for 1 hour. The white solid which formed was separated by filtration, washed with aqueous 2-propanol and vacuum oven dried to give the ammonium salt of 3-(1H-tetrazol-5-yl)-4(3H)-quinazolinone.

EXAMPLE 13

A cooled (0° C.) slurry was prepared from 10 g of $N^1$-(1H-tetrazol-5-yl)-$N^2$-(2-carbomethoxyphenyl)formamidine and 25 ml of water and this was stirred while 8.2 ml of 5N sodium hydroxide was added dropwise. The mixture was brought to room temperature and 200 ml of 2-propanol was added. It was then heated to 70° C., a further 90 ml of 2-propanol was added, and the mixture was stirred for 4 hours at 70° C. It was then cooled to room temperature and stirred for 16 hours. The white crystals which formed were separated by filtration and washed with aqueous 2-propanol and vacuum oven dried to give the sodium salt of 3-(1H-tetrazol-5-yl)-4(3H)-quinazolinone.

EXAMPLE 14

A solution was prepared from 0.3 g of $N^1$-(1H-tetrazol-5-yl)-$N^2$-(2-carbomethoxyphenyl)formamidine and 10 ml of N,N-dimethylformamide. A slurry of 67 mg of sodium methoxide in 1.4 ml of N,N-dimethylformamide was added and the mixture was stirred under nitrogen for 30 minutes. The solvent was then evaporated under reduced pressure to give the sodium salt of 3-(1H-tetrazol-5-yl)-4(3H)-quinazolinone.

EXAMPLE 15

A mixture was prepared from 0.3 g of $N^1$-(1H-tetrazol-5-yl)-$N^2$-(2-carbomethoxyphenyl)formamidine and 15 ml of methanol and cooled to 0° C. under positive pressure of nitrogen. Solid sodium methoxide (0.66 g) was added portionwise and the mixture was stirred for 15 minutes. The solvent was evaporated in vacuo to give crude sodium salt of 3-(1H-tetrazol-5-yl)-4(3H)-quinazolinone (93% pure by HPLC).

EXAMPLE 16

A mixture was prepared from 0.4 g of $N^1$-(1H-tetrazol-5-yl)-$N^2$-(2-carbomethoxyphenyl)formamidine and 40 ml of toluene and this was heated to 60° C. under nitrogen. A solution of 20% sodium t-butoxide in tetrahydrofuran (0.7 ml) was added, the mixture was stirred at 60° C. for 1 hour, and then cooled to room temperature. The off-white solid which formed was separated by filtration, washed with hexane and vacuum oven dried to give crude sodium salt of 3-(1H-tetrazol-5-yl)-4(3H)-quinazolinone with a purity of greater than 90% as shown by HPLC.

EXAMPLE 17

$N^1$-(1H-Tetrazol-5-yl)-$N^2$-(2-carbomethoxyphenyl)-formaidine (5 g) was mixed with 25 ml of 2-propanol. The resulting slurry was stirred at room temperature and 2 g of triethylamine was added. The mixture was heated at reflux for 24 hours and then cooled to room temperature. The white crystals which formed were separated by filtration, washed with 2-propanol and dried to give the triethylammonium salt of 3-(1H-tetrazol-5-yl)-4(3H)-quinazolinone melting at about 112°–115° C. Evaporation of the solvent from the filtrate in vacuo gave a residue which was triturated with carbon tetrachloride, filtered and dried to give additional crude triethylammonium salt.

EXAMPLE 18

A mixture was prepared from 10 g of 5-aminotetrazole, 18.2 g of triethoxymethane, 18 g of methyl anthranilate and 90 ml of 2-propanol and this was heated at 70° C. under nitrogen and stirred for 1.5 hours. The mixture was then cooled to room temperature, 23 ml of distilled water was added, and the resulting mixture was then stirred for 15 minutes before 24 ml of 5N aqueous sodium hydroxide was added. The resulting mixture was first stirred at room temperature for 15 minutes and then heated to reflux. A clear pale yellow solution resulted and 180 ml of 2-propanol was added at such a rate that the temperature remained above 70° C. Reflux was then maintained for 1 hour before the mixture was cooled to room temperature with stirring. Crystallization took place during this time and the crystals which formed were separated by filtration, washed with 2-propanol and dried in a vacuum oven to give the sodium salt of 3-(1H-tetrazol-5-yl)-4(3H)-quinazolinone melting at greater than 300° C. The purity of the product, as determined by HPLC, was greater than 99.9% and the yield was 80% as the trihydrate. The product can be isolated as the trihydrate, in anhydrous form, or as some intermediate hydrate, depending on the duration and amount of heating used in the drying process.

EXAMPLE 19

A mixture of 5 g of 5-aminotetrazole, 9.8 g of triethoxymethane, 9.9 g of methyl anthranilate and 50 ml of carbon tetrachloride was prepared and heated at reflux under nitrogen for 16 hours. Anhydrous sodium carbonate (3.1 g) was added to the hot mixture followed by the slow addition of 50 ml of distilled water. The mixture was then stirred for 30 minutes, cooled to room temperature and filtered to remove solid materials. The aqueous layer was then separated and it was heated to 75° C. To this hot solution was added 100 ml of 2-propanol while maintaining the temperature above 70° C. Reflux was continued for an additional 30 minutes and the mixture was then cooled to room temperature. The crystals which formed were separated by filtration, washed with 2-propanol and dried to give the sodium salt of 3-(1H-tetrazol-5-yl)-4(3H)-quinazolinone·2.7 hydrate.

EXAMPLE 20

A solution was prepared from 10 g of 5-aminotetrazole and 100 ml of N,N-dimethylformamide and heated to 90° C. Triethoxymethane (21.3 g) was added and the mixture was stirred at 90° C. under nitrogen for 3 hours. A solution of 16 g of anthranilamide in 20 ml of N,N-dimethylformamide was then added, the resulting mixture was cooled to 85° C., and then it was stirred at 85° C. for 1 hour. The mixture was cooled to room temperature over 16 hours during which time crystallization took place. The crystals which formed were separated by filtration to give 2.3 g of product and the filtrate was concentrated to give a further 5.3 g of product. The solid obtained in this way was the ammonium salt of 3-(1H-tetrazol-5-yl)-4(3H)-quinazolinone melting at about 236°–240° C.

EXAMPLE 21

A slurry of 0.5 g of the ammonium salt of 3-(1H-tetrazol-5-yl)-4(3H)-quinazolinone in 10 ml of methanol was stirred at room temperature, acidified with 0.7 ml of 3N hydrochloric acid, and stirred for 15 minutes. 2-Propanol (5 ml) was added and the resulting mixture was stirred for an additional 15 minutes. The white powdery crystalline solid which formed was collected by filtration, washed with cold methanol and dried to give 3-(1H-tetrazol-5-yl)-4(3H)-quinazolinone which was identical with the material prepared according to the procedure described in the prior art.

EXAMPLE 22

A mixture was prepared from 10 g of 5-aminotetrazole and 50 ml N,N-dimethylformamide. This was heated to 100° C. and 17 g of triethoxymethane was added. The resulting mixture was stirred at 100° C. under nitrogen for 2 hours and then a solution of the ammonium salt of anthranilic acid (prepared from 16 g of anthranilic acid and 7.8 ml of 14.8M ammonium hydroxide in methanol, followed by removal of the methanol) in 40 ml of N,N-dimethylformamide was added. The mixture was stirred for 1 hour at 100° C., then cooled to room temperature and finally cooled in an ice bath to induce crystallization. The white crystals which formed were separated by filtration, washed with N,N-dimethylformamide and then with carbon tetrachloride, and vacuum oven dried to give the ammonium salt of 3-(1H-tetrazol-5-yl)4(3H)-quinazolinone.

EXAMPLE 23

A solution was prepared from 11.7 g of methyl anthranilate and 80 ml of anhydrous methanol and cooled to 0° C. under nitrogen. To this stirred solution was added 10 g of 5-(ethoxymethyleneamino)tetrazole as a solid. The reaction mixture was stirred for 20 minutes and then 14.2 ml of 5N sodium hydroxide was added and stirring was continued for 10 minutes. The mixture was filtered to remove some insoluble solid and the solvent was evaporated from the filtrate in vacuo to leave a residual glassy solid. This was taken up in water/2-propanol (35 ml, 1:1) and heated to 70° C. An additional 80 ml of 2-propanol was added and heating was continued for 20 minutes. The mixture was then allowed to cool to room temperature over 16 hours. The crystals which formed were separated by filtration, washed with aqueous 2-propanol and vacuum oven dried to give the sodium salt of 3-(1H-tetrazol-5-yl)-4(3H)-quinazolinone hydrate.

EXAMPLE 24

A mixture of 10.1 g of 5-aminotetrazole monohydrate, 60 g of triethoxymethane and 155 ml of hexane was heated under nitrogen until distillate appeared. Slow distillation was continued for 7 hours (head temperature 60°-80° C.) with hexane added to replenish the material removed. To the hot mixture was added 14.8 g of methyl anthranilate and, after 1.5 hours, the mixture was allowed to cool to room temperature and stirred for 48 hours. To the resulting mixture was added 80 ml of methanol followed by slow addition of sufficient 5N sodium hydroxide to bring the pH to approximately 8. The mixture was then stirred briefly and the white solid was separated by filtration, washed with aqueous 2-propanol and vacuum oven dried to give the sodium salt of 3-(1H-tetrazol-5-yl)-4(3H)-quinazolinone.

EXAMPLE 25

A mixture was prepared from 12 g of 5-aminotetrazole monohydrate, 36.5 g of triethoxymethane, 38.5 g of methyl anthranilate and 100 ml of ethyl acetate under a positive pressure of nitrogen. The mixture was heated at 60° C. for 6 hours and then 50 ml of 2.3N sodium hydroxide was added to the hot solution. Agitation was discontinued to allow phase separation and the organic phase was removed. To the hot aqueous phase was added 300 ml of 2-propanol and this mixture was stirred for 2 hours as precipitation occurred. The mixture was cooled for 16 hours and the white crystals were separated by filtration, washed with aqueous 2-propanol and vacuum oven dried to give the sodium salt of 3-(1H-tetrazol-5-yl)-4(3H)-quinazolinone which was identical with authentic material.

EXAMPLE 26

Under a positive pressure of nitrogen, a mixture was prepared from 10 g of 5-aminotetrazole, 19.6 g of triethoxymethane, 19.8 g of methyl anthranilate and 150 ml of toluene. This heterogeneous mixture was heated until distillate appeared and slow distillation was continued for 5 hours with replenishment of the toluene in the reaction vessel as necessary. The mixture was then cooled to 65° C. and 6.4 g of anhydrous sodium carbonate was added followed by the slow addition of 50 ml of water. The mixture was then heated for 30 minutes and the aqueous phase was separated. This aqueous phase was heated to 80° C. and to the hot mixture was slowly added 300 ml of 2-propanol. This mixture was stirred at 80° C. for 30 minutes, then cooled to room temperature and stirred for 12 hours. The white crystalline solid which formed was separated by filtration, washed with aqueous 2-propanol and vacuum oven dried to give the sodium salt of 3-(1H-tetrazol-5-yl)-4(3H)-quinazolinone trihydrate which was identical with authentic material.

When the procedures described above are repeated using substituted anthranilic acid derivatives or other anthranilic acid esters, the corresponding 4(3H)-quinazolinones are obtained.

What is claimed is:

1. A process for the preparation of a quinazolinone compound of the formula

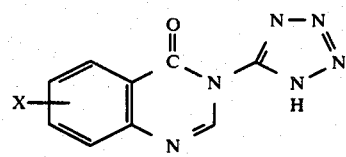

wherein X represents hydrogen or one or two methyl, halogen or methoxy groups or a methylenedioxy group, and the alkali metal, ammonium and amine salts thereof, which comprises:

(a) reacting an anthranilic acid derivative of the formula

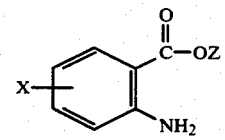

wherein X is defined as above and Z is alkyl of 1–4 carbon atoms or ammonium or OZ is $NH_2$, with a 5-(alkoxymethyleneamino)tetrazole which has the structural formula

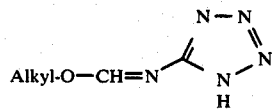

wherein the Alkyl group contains 1 to 4 carbon atoms, in an inert solvent to give a formamidine of the formula

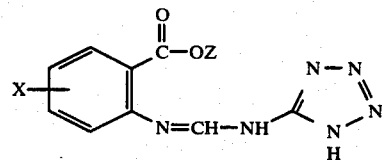

(b) cyclizing said formamidine to the quinazolinone product directly when Z or OZ contains nitrogen or, when Z is alkyl of 1–4 carbon atoms, by the use of an alkali metal base, ammonium hydroxide or an amine and, (c) when the cyclization product is obtained in the form of a salt and the free tetrazole is desired, acidifying said cyclization product with a mineral acid to give the desired quinazolinone.

2. A process according to claim 1 for the preparation of a quinazolinone compound of the formula

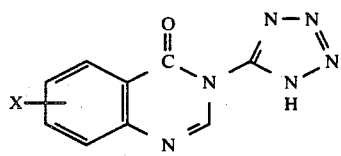

wherein X represents hydrogen or one or two methyl, halogen or methoxy groups or a methylenedioxy group, and the alkali metal, ammonium or amine salts thereof, which comprises:

(a) reacting an anthranilic acid ester of the formula

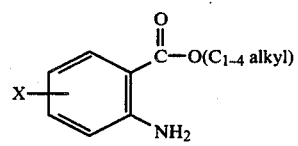

wherein X is defined as above, with 5-(ethoxymethylenemino)tetrazole in an inert solvent to give a formamidine of the formula

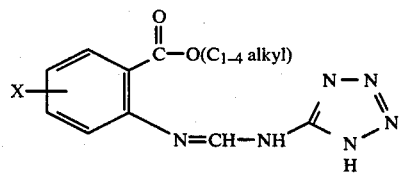

(b) cyclizing said formamidine to the quinazolinone product tetrazole salt by the use of an alkali metal base, ammonium hydroxide or an amine and, (c) when the free tetrazole is desired, acidifying said cyclization product with a mineral acid to give the desired quinazolinone.

3. A process according to claim 1 for the preparation of a quinazolinone compound of the formula

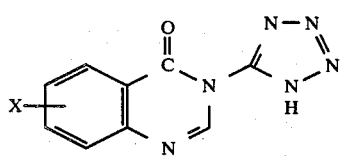

wherein X represents hydrogen or one or two methyl, halogen or methoxy groups or a methylenedioxy group, and the alkali metal and ammonium salts thereof, which comprises:

(a) reacting an anthranilic acid methyl ester of the formula

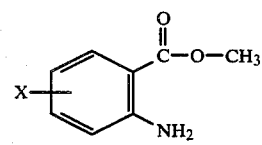

wherein X is defined as above, with 5-(ethoxymethyleneamino)tetrazole in an inert solvent to give a formamidine of the formula

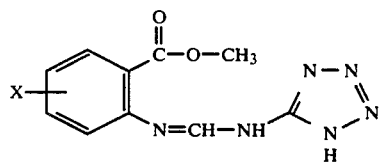

(b) cyclizing said formamidine to the quinazolinone product tetrazole salt by the use of an alkali metal base or ammonium hydroxide and, (c) when the free tetrazole is desired, acidifying said cyclization product with a mineral acid to give the desired quinazolinone.

4. A process according to claim 1 for the preparation of 3-(1H-tetrazol-5-yl)-4(3H)-quinazolinone and the alkali metal and ammonium salts thereof, which comprises:

(a) reacting methyl anthranilate with 5-(ethoxymethyleneamino)tetrazole in an inert solvent to give a formamidine of the formula

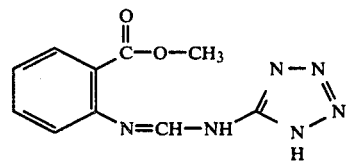

(b) cyclizing said formamidine to the 3-(1H-tetrazol-5-yl)-4(3H)-quinazolinone salt by the use of an alkali metal base or ammonium hydroxide and, (c) when the free tetrazole is desired, acidifying said cyclization product with a mineral acid to give 3-(1H)-tetrazol-5-yl)-4(3H)-quinazolinone.

5. A process according to claim 1 for the preparation of the sodium salt of 3-(1H)-tetrazol-5-yl)-4(3H)-quinazolinone which comprises:

(a) reacting methyl anthranilate with 5-(ethoxymethyleneamino)tetrazole in an inert solvent to give a formamidine of the formula

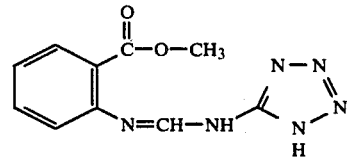

(b) cyclizing said formamidine to the sodium salt of 3-(1H-tetrazol-5-yl)-4(3H)-quinazolinone by the use of sodium hydroxide.

6. A process according to claim 1 for the preparation of 3-(1H-tetrazol-5-yl)-4(3H)-quinazolinone which comprises:

(a) reacting methyl anthranilate with 5-(ethoxymethyleneamino)tetrazole in an inert solvent to give a formamidine of the formula

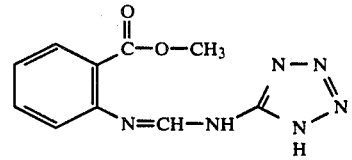

(b) cyclizing said formamidine to the sodium salt of 3-(1H-tetrazol-5-yl)-4(3H)-quinazolinone by the use of sodium hydroxide and, (c) acidifying said sodium salt with a hydrochloric acid to give the desired 3-(1H-tetrazol-5-yl)-4(3H)-quinazolinone.

7. A process according to claim 1 for the preparation of 3-(1H-tetrazol-5-yl)-4(3H)-quinazolinone and the alkali metal, ammonium or amine salts thereof which comprises mixing methyl anthranilate, 5-aminotetrazole and triethoxymethane in an inert solvent followed by the addition of a base selected from an alkali metal base, ammonium hydroxide or an amine to give the desired salt products, optionally followed by acidification of the salt formed by means of a mineral acid when the free tetrazole is desired.

8. A process according to claim 1 for the preparation of the sodium salt of 3-(1H-tetrazol-5-yl)4(3H)-quinazolinone which comprises mixing methyl anthranilate, 5-aminotetrazole and triethoxymethane in an inert solvent followed by the addition of sodium hydroxide.

9. A process according to claim 1 for the preparation of 3-(1H-tetrazol-5-yl)-4(3H)-quinazolinone which comprises mixing methyl anthranilate, 5-aminotetrazole and triethoxymethane in an inert solvent followed by the addition of sodium hydroxide to give the sodium salt of 3-(1H-tetrazol-5-yl)-4(3H)-quinazolinone followed by acidification of the salt with hydrochloric acid.

10. 5-(Ethoxymethyleneamino)tetrazole.

11. $N^1$-(1H-tetrazol-5-yl)-$N^2$-(2-carbomethoxyphenyl)formamidine.

* * * * *